(12) United States Patent
Suto

(10) Patent No.: US 12,398,088 B2
(45) Date of Patent: Aug. 26, 2025

(54) METHOD FOR PRODUCING AROMATIC BIS ETHER COMPOUND

(71) Applicant: HONSHU CHEMICAL INDUSTRY CO., LTD., Tokyo (JP)

(72) Inventor: Takeru Suto, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 775 days.

(21) Appl. No.: 17/640,793

(22) PCT Filed: Sep. 15, 2020

(86) PCT No.: PCT/JP2020/034836
§ 371 (c)(1),
(2) Date: Mar. 4, 2022

(87) PCT Pub. No.: WO2021/054309
PCT Pub. Date: Mar. 25, 2021

(65) Prior Publication Data
US 2022/0324789 A1 Oct. 13, 2022

(30) Foreign Application Priority Data
Sep. 20, 2019 (JP) .................................. 2019-172079

(51) Int. Cl.
*C07C 67/31* (2006.01)

(52) U.S. Cl.
CPC .................... *C07C 67/31* (2013.01)

(58) Field of Classification Search
CPC ......... C07C 67/31; C07C 69/72; C07C 51/02; C07C 59/66
See application file for complete search history.

(56) References Cited

FOREIGN PATENT DOCUMENTS

| CN | 105198839 A | 12/2015 | | |
|----|----|----|----|----|
| CN | 109232860 A | 1/2019 | | |
| CN | 110028652 | * 7/2019 | ............. | C08G 59/06 |
| CN | 110028652 A | 7/2019 | | |
| CN | 113329989 A | 8/2021 | | |
| CN | 113891875 A | 1/2022 | | |
| EP | 3805195 A1 | 4/2021 | | |
| EP | 4001251 A1 | 5/2022 | | |

(Continued)

OTHER PUBLICATIONS

A First Office Action issued by the State Intellectual Property Office of China on Apr. 22, 2023, for Chinese counterpart application No. 202080062513.9 (6 pages).

(Continued)

*Primary Examiner* — Yate' K Cutliff
(74) *Attorney, Agent, or Firm* — Law Office of Katsuhiro Arai

(57) ABSTRACT

An object is to provide a new method for producing an aromatic bis ether compound in an industrially stable manner and in high yield. As a solution, a method for producing an aromatic bis ether compound represented by formula (3), in which in a reaction between an aromatic dihydroxy compound (1) represented by formula (1) above and a halide (2) represented by formula (2) above, the amount of water in a reaction solution is 0.01 wt % or more and 1.5 wt % or less relative to the amount of the aromatic dihydroxy compound (1) in the reaction solution, is provided.

1 Claim, 1 Drawing Sheet

(56) References Cited

FOREIGN PATENT DOCUMENTS

| JP | 2008024650 A | 2/2008 |
| JP | 2009067681 A | 4/2009 |
| JP | 2015101605 A | 6/2015 |
| JP | 2018059074 A | 4/2018 |
| WO | 2019230685 A1 | 12/2019 |
| WO | 2020171039 A1 | 8/2020 |

OTHER PUBLICATIONS

Jia et al., A chiral BINOL-based Gemini amphiphilic gelator and its specific discrimination of native arginine by gelation in water, SoftMatter, 2017, 13, 5453-5462.

Ema et al., Synthesis and evaluation of chiral selectors with multiple hydrogen-bonding sites in the macrocyclic cavities, J. Org. Chem. 2010, Jun. 1, 2010, 4492-4500, vol. 75, No. 13. (9 pages).

International Search Report (ISR) mailed Nov. 2, 2020, issued for International application No. PCT/JP2020/034836. (3 pages).

A Second Office Action issued by the State Intellectual Property Office of China on Mar. 16, 2024, for Chinese counterpart application No. 202080062513.9 (7 pages).

Zhang, Organic Chemistry Class Notes, People's Army Medical Press, Jan. 2011, 1st edition, 1st printing, p. 92 (5 pages).

\* cited by examiner

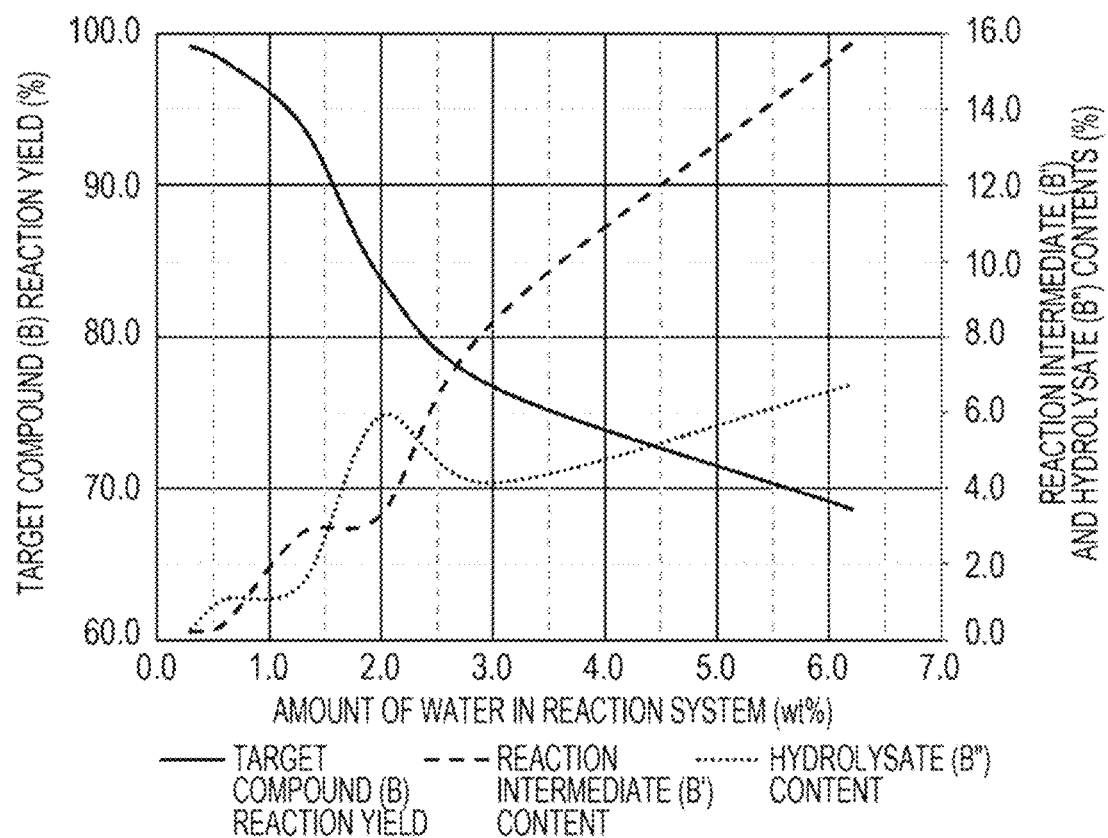

METHOD FOR PRODUCING AROMATIC BIS ETHER COMPOUND

CROSS-REFERENCE TO RELATED APPLICATIONS

This application is the U.S. National Phase under 35 U.S.C. § 371 of International Application PCT/JP2020/034836, filed Sep. 15, 2020, which claims priority to Japanese Patent Application No. JP2019-172079, filed Sep. 20, 2019. The International Application was published under PCT Article 21 (2) in a language other than English.

TECHNICAL FIELD

The present invention relates to a method for producing an aromatic bis ether compound.

BACKGROUND ART

Polyester resins and polyester carbonate resins produced using dicarboxylic acid components having an aromatic bis ether skeleton as polymerization components have excellent optical properties such as high refractive indices and low birefringence and have high levels of heat resistance, and thus have recently been expected to be materials for optical members such as optical disks, transparent conductive substrates, and optical filters.

As methods for synthesizing dicarboxylic acid components having an aromatic bis ether skeleton, many methods involving reacting an aromatic dihydroxy compound and a halogen compound with each other are known. For example, it has been reported that 2,2'-bis(2-ethoxycarbonylmethoxy)-1,1'-binaphthyl can be obtained by reacting 1,1'-binaphthalene-2,2'-diol and a halogenated acetate ester such as ethyl chloroacetate with each other (PTLs 1 and 2).

CITATION LIST

Patent Literature

PTL 1: Japanese Unexamined Patent Application Publication No. 2018-059074
PTL 2: Japanese Unexamined Patent Application Publication No. 2008-024650

SUMMARY OF INVENTION

Technical Problem

In the related art including PTLs 1 and 2 above, no studies have been made on the assumption of industrial production of an aromatic bis ether compound according to the present invention.

On the other hand, when the present inventors industrially produced an aromatic bis ether compound according to the present invention in succession, the amount of impurities unfortunately increased, resulting in a decrease in the yield of the target compound.

The present inventors consider this decrease in the yield of the target compound as follows. In a reaction using an inorganic base such as potassium carbonate to industrially produce an aromatic bis ether compound, it is necessary to perform water washing after the reaction in order to remove the inorganic base. If this water washing operation is performed in the same reaction vessel where the reaction has been carried out, a certain amount of water may remain in the reaction vessel, and if the reaction is industrially carried out in succession, the amount of water in the reaction system at the second and subsequent runs will increase.

The present invention has been made in view of the foregoing circumstances, and an object thereof is to provide a new method for producing an aromatic bis ether compound in an industrially stable manner and in high yield.

Solution to Problem

The present inventors have focused on the water remaining in the reaction vessel and studied the influence of the amount of water in the reaction system on reaction results, and have confirmed for the first time that when the reaction is carried out in a state where the amount of water has increased, a decrease in the yield of the target compound actually occurs due to a slowdown of the etherification reaction rate and an increase in impurities.

The present inventors have found that by controlling the amount of water in a reaction solution to be in a specific range, an aromatic bis ether compound can be produced in an industrially stable manner and in high yield, thereby completing the present invention.

The present invention is as follows.
1. A method for producing an aromatic bis ether compound represented by formula (3) below, in which in a reaction between an aromatic dihydroxy compound (1) represented by formula (1) below and a halide (2) represented by formula (2) below, the amount of water in a reaction solution is 0.01 wt % or more and 1.5 wt % or less relative to the amount of the aromatic dihydroxy compound (1) in the reaction solution.

[Chem. 1]

(1)

(In formula (1), $Ar_1$ and $Ar_2$ each independently represent an aryl group having 6 to 12 carbon atoms, each $R_1$ independently represents a linear or branched alkyl group having 1 to 6 carbon atoms or a cyclic alkyl group having 5 or 6 carbon atoms, each n independently represents an integer of 0 to 4, and X represents a single bond, an oxygen atom, a sulfur atom, a sulfonyl group, a carbonyl group, or a divalent group represented by formula (1a) or (1b) below.)

[Chem. 2]

(1a)

(1b)

(In formulae (1a) and (1b), $R_2$ and $R_3$ each independently represent hydrogen, an alkyl group having 1 to 10 carbon atoms, an alkyl halide group having 1 to 10 carbon atoms, or an aryl group having 6 to 12 carbon atoms, $R_2$ and $R_3$ may be bonded to each other to form a cycloalkylidene group having 5 to 20 carbon atoms, $Ar_3$ and $Ar_4$ each independently represent an aryl group having 6 to 12 carbon atoms, and * represents a bonding position.)

[Chem. 3]

Y-A  (2)

(In formula (2), Y represents a halogen atom, and A represents a linear or branched alkyl group having 1 to 10 carbon atoms, a cyclic alkyl group having 1 to 10 carbon atoms, or a group selected from groups represented by formulae (2a) to (2d) below.)

[Chem. 4]

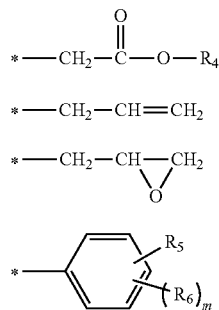

(2a)

(2b)

(2c)

(2d)

(In formula (2a), $R_4$ represents a linear or branched alkyl group having 1 to 6 carbon atoms, and in formula (2d), $R_5$ represents a hydroxy group, a nitro group, an amino group, or a vinyl group, $R_6$ represents a linear or branched alkyl group having 1 to 10 carbon atoms, a cyclic alkyl group having 1 to 10 carbon atoms, or a perfluoroalkyl group having 1 to 10 carbon atoms, m represents an integer of 0 to 4, and * represents a bonding position.)

[Chem. 5]

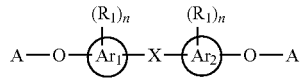

(3)

(In formula (3), $Ar_1$, $Ar_2$, $R_1$, n, X, and A are as defined in formulae (1) and (2).)

Advantageous Effects of Invention

According to the present invention, an aromatic bis ether compound can be produced in an industrially stable manner, and the target compound can be obtained in high yield.

That is, the provision of the production method of the present invention is very useful in industrial production of resin raw materials and the like.

BRIEF DESCRIPTION OF DRAWING

FIG. 1 is a graph showing the relationships in Examples 1 to 3 and Comparative Examples 1 to 3 between the amount of water in a reaction system relative to the amount of a compound represented by general formula (1) used and the reaction yield of a compound represented by general formula (3), the content of a reaction intermediate (B'), and the content of a hydrolysate (B").

DESCRIPTION OF EMBODIMENTS

Hereinafter, the present invention will be described in detail.

A production method of the present invention is a method represented by the following reaction formula.

[Chem. 6]

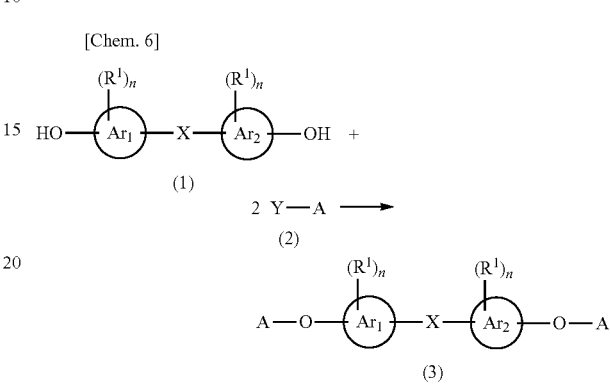

(In the formula, $Ar_1$, $Ar_2$, $R_1$, n, X, Y, and A are as defined in formulae (1) and (2).)

<Aromatic Dihydroxy Compound (1)>

One of the starting materials used in the production method of the present invention is an aromatic dihydroxy compound represented by formula (1) below (hereinafter referred to as the "aromatic dihydroxy compound (1)").

[Chem. 7]

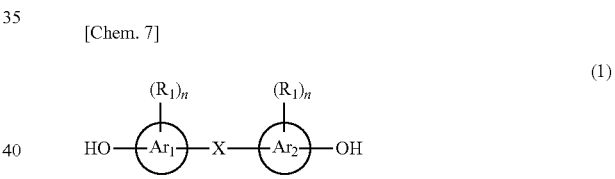

(1)

(In formula (1), $Ar_1$ and $Ar_2$ each independently represent an aryl group having 6 to 12 carbon atoms, each $R_1$ independently represents a linear or branched alkyl group having 1 to 6 carbon atoms or a cyclic alkyl group having 5 or 6 carbon atoms, each n independently represents an integer of 0 to 4, and X represents a single bond, an oxygen atom, a sulfur atom, a sulfonyl group, a carbonyl group, or a divalent group represented by formula (1a) or (1b) below.)

[Chem. 8]

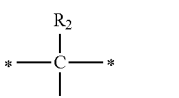

(1a)

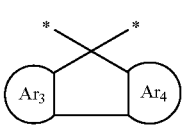

(1b)

(In formulae (1a) and (1b), $R_2$ and $R_3$ each independently represent hydrogen, an alkyl group having 1 to 10 carbon atoms, an alkyl halide group having 1 to 10 carbon atoms, or an aryl group having 6 to 12 carbon atoms, $R_2$ and $R_3$ may be bonded to each other to form a cycloalkylidene group having 5 to 20 carbon atoms, $Ar_3$ and $Ar_4$ each independently represent an aryl group having 6 to 12 carbon atoms, and * represents a bonding position.)

$Ar_1$ and $Ar_2$ in formula (1) above each independently represent an aryl group having 6 to 12 carbon atoms, and specific examples include a phenylene group, a naphthylene group, and a biphenylene group. Among them, a phenylene group and a naphthylene group are preferred, and particularly preferably, $Ar_1$ and $Ar_2$ are each a naphthylene group.

$R_1$ in formula (1) above represents a linear or branched alkyl group having 1 to 6 carbon atoms or a cyclic alkyl group having 5 or 6 carbon atoms. In particular, linear or branched alkyl groups having 1 to 6 carbon atoms such as a methyl group, an ethyl group, a n-propyl group, an isopropyl group, a n-butyl group, a t-butyl group, a n-pentyl group, a 2-methylpentyl group, and a n-hexyl group are preferred, and a methyl group and an ethyl group are more preferred.

n in formula (1) above represents an integer of 0 to 4, and is preferably an integer of 0 to 3, more preferably an integer of 0 to 2, still more preferably 0 or 1, particularly preferably 0.

X in formula (1) above is preferably a single bond or a divalent group represented by formula (1a) or formula (1b), more preferably a single bond or a divalent group represented by formula (1a), particularly preferably a single bond.

When X in formula (1) above is a single bond, the aromatic dihydroxy compound (1) is represented by formula (1-1) below.

[Chem. 9]

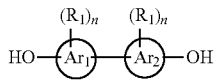

(1-1)

(In the formula, $Ar_1$, $Ar_2$, $R_1$, and n are as defined in formula (1).)

Furthermore, when $Ar_1$ and $Ar_2$ are each a phenylene group, the aromatic dihydroxy compound (1) is represented by formula (1-2) below.

[Chem. 10]

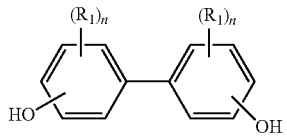

(1-2)

(In the formula, $R_1$ and n are as defined in formula (1).)

The bonding position of OH groups in formula (1-2) above is preferably ortho or para, particularly preferably para, to the bonding position between the phenylene groups.

The bonding position of groups represented by $R_1$ in formula (1-2) above is preferably meta to the bonding position between the phenylene groups.

When $Ar_1$ and $Ar_2$ in formula (1-1) above are each a naphthylene group, the aromatic dihydroxy compound (1) is represented by formula (1-3) below.

[Chem. 11]

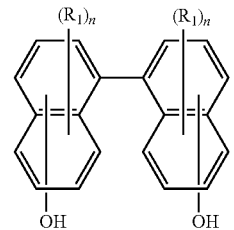

(1-3)

(In the formula, $R_1$ and n are as defined in formula (1).)

The bonding position of OH groups in formula (1-3) above is preferably the 2-position or 4-position, particularly preferably the 2-position, with respect to the bonding position between the naphthylene groups.

The bonding position of groups represented by $R_1$ in formula (1-3) above is preferably the 3-position or 6-position, more preferably the 3-position, with respect to the bonding position between the naphthylene groups.

One example of the compound represented by formula (1-1) above in the case where $Ar_1$ and $Ar_2$ are each a biphenylene group is 3,3'-diphenyl-biphenyl-4,4'-diol.

Specific examples of the aromatic dihydroxy compound (1) in the present invention include biphenyl-4,4'-diol, 3,3'-dimethyl-biphenyl-4,4'-diol, 3,3'-diethyl-biphenyl-4,4'-diol, 3,3',5,5'-tetramethyl-biphenyl-4,4'-diol, 3,3',6,6'-tetramethyl-biphenyl-4,4'-diol, 3,3'-dimethyl-5,5'-di-t-butyl-biphenyl-4,4'-diol, 3,3',5,5'-tetra-t-butyl-biphenyl-4,4'-diol, 1,1'-binaphthalene-2,2'-diol, 2,2'-binaphthalene-1,1'-diol, and 3,3'-diphenyl-biphenyl-4,4'-diol. Among them, biphenyl-4,4'-diol, 3,3'-dimethyl-biphenyl-4,4'-diol, 3,3',5,5'-tetramethyl-biphenyl-4,4'-diol, and 1,1'-binaphthalene-2,2'-diol are preferred, and 1,1'-binaphthalene-2,2'-diol, which is represented by formula (A) below, is particularly preferred.

[Chem. 12]

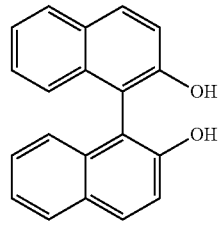

(A)

When X in formula (1) above is formula (1a), each of $R_2$ and $R_3$ is more preferably hydrogen, an alkyl group having 1 to 6 carbon atoms, an alkyl halide group having 1 to 6 carbon atoms, or an aryl group having 6 to 12 carbon atoms, still more preferably hydrogen, an alkyl group having 1 to 4 carbon atoms, a trifluoromethyl group, or an aryl group having 6 to 8 carbon atoms, particularly preferably hydrogen, an alkyl group having 1 to 4 carbon atoms, or a phenyl group. $R_2$ and $R_3$ may be bonded to each other to form a cycloalkylidene group having 5 to 20 carbon atoms. The cycloalkylidene group having 5 to 20 carbon atoms may include an alkyl group as a branched chain. The cycloalkylidene group preferably has 5 to 15 carbon atoms, more preferably has 6 to 12 carbon atoms, and particularly preferably has 6 to 9 carbon atoms. Specific examples of the cycloalkylidene group include a cyclopentylidene group (5 carbon atoms), a cyclohexylidene group (6 carbon atoms), a 3-methylcyclohexylidene group (7 carbon atoms), a 4-methylcyclohexylidene group (7 carbon atoms), a 3,3,5-trimethylcyclohexylidene group (9 carbon atoms), a cycloheptylidene group (7 carbon atoms), and a cyclododecanylidene group (12 carbon atoms). The cycloalkylidene group is preferably a cyclohexylidene group (6 carbon atoms), a 3-methylcyclohexylidene group (7 carbon atoms), a 4-methylcyclohexylidene group (7 carbon atoms), a 3,3,5-trimethylcyclohexylidene group (9 carbon atoms), or a cyclododecanylidene group (12 carbon atoms), more preferably a cyclohexylidene group (6 carbon atoms), a 3,3,5-trimethylcyclohexylidene group (9 carbon atoms), or a cyclododecanylidene group (12 carbon atoms).

In formula (1b) above, $Ar_3$ and $Ar_4$ are preferably each independently a benzene ring or a naphthalene ring, and $Ar_3$ and $Ar_4$ are more preferably each a benzene ring. For example, when $Ar_3$ and $Ar_4$ are each a benzene ring, the group represented by formula (1b) is a fluorenylidene group.

<Halide (2)>

One of the starting materials used in the production method of the present invention is a halide represented by formula (2) below (hereinafter referred to as the "halide (2)").

[Chem. 13]

$$Y-A \quad (2)$$

(In formula (2), Y represents a halogen atom, and A represents a linear or branched alkyl group having 1 to 10 carbon atoms, a cyclic alkyl group having 1 to 10 carbon atoms, or a group selected from groups represented by formulae (2a) to (2d) below.)

[Chem. 14]

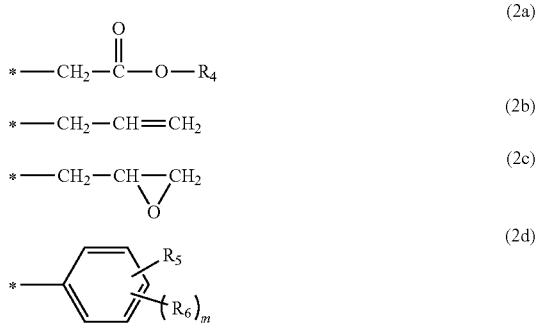

(2a)

(2b)

(2c)

(2d)

(In formula (2a), $R_4$ represents a linear or branched alkyl group having 1 to 6 carbon atoms, and in formula (2d), $R_5$ represents a hydroxy group, a nitro group, an amino group, or a vinyl group, $R_6$ represents a linear or branched alkyl group having 1 to 10 carbon atoms, a cyclic alkyl group having 1 to 10 carbon atoms, or a perfluoroalkyl group having 1 to 10 carbon atoms, m represents an integer of 0 to 4, and * represents a bonding position.)

In formula (2) above, Y represents a halogen atom, and specific examples include a fluorine atom, a chlorine atom, a bromine atom, and an iodine atom, among which a chlorine atom and a bromine atom are preferred, and a chlorine atom is particularly preferred.

In formula (2) above, the linear or branched alkyl group having 1 to 10 carbon atoms represented by A is more preferably a linear or branched alkyl group having 1 to 4 carbon atoms, still more preferably a linear alkyl group having 1 to 4 carbon atoms, particularly preferably a methyl group. Specific examples of the cyclic alkyl group having 5 to 10 carbon atoms represented by A include a cyclopentyl group, a cyclohexyl group, a cycloheptyl group, a cyclooctyl group, a 1-adamantyl group, and a 2-adamantyl group.

$R_4$ in formula (2a) above is more preferably a linear or branched alkyl group having 1 to 4 carbon atoms, still more preferably a primary or secondary alkyl group having 1 to 4 carbon atoms, particularly preferably an ethyl group.

Specific examples of the compound (2) in the case where A is a group represented by formula (2a) include methyl chloroacetate, ethyl chloroacetate, propyl chloroacetate, methyl bromoacetate, ethyl bromoacetate, propyl bromoacetate, methyl iodoacetate, ethyl iodoacetate, and propyl iodoacetate.

$R_5$ in formula (2d) above is a hydroxy group, a nitro group, an amino group, or a vinyl group, more preferably an amino group. $R_6$ is more preferably an alkyl group having 1 to 6 carbon atoms, an alkyl halide group having 1 to 6 carbon atoms, or an aryl group having 6 to 12 carbon atoms, still more preferably an alkyl group having 1 to 4 carbon atoms, a trifluoromethyl group, or an aryl group having 6 to 8 carbon atoms, particularly preferably a methyl group, a trifluoromethyl group, or a phenyl group. m represents an integer of 0 to 4, and is preferably an integer of 0 to 3, more preferably an integer of 0 to 2, still more preferably 0 or 1, particularly preferably 0.

The substitution position of $R_5$ in formula (2d) above is preferably para or meta, particularly preferably para, to the bonding position represented by *. When the substitution position of $R_5$ is para to the bonding position represented by *, $R_6$ is preferably ortho to the bonding position represented by *, and when the substitution position of $R_5$ is meta to the bonding position represented by *, $R_6$ is preferably para to the bonding position represented by *.

Preferred examples of formula (2d) above include the following groups.

[Chem. 15]

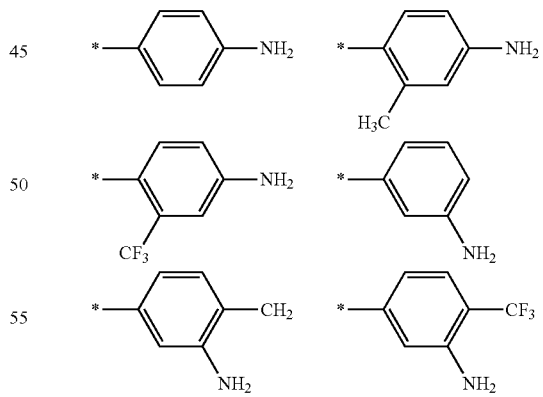

A in formula (2) above is particularly preferably a group represented by formula (2a).

<Aromatic Bis Ether Compound (3)>

The target compound in the production method of the present invention is an aromatic bis ether compound represented by formula (3) below (hereinafter referred to as the "aromatic bis ether compound (3)").

[Chem. 16]

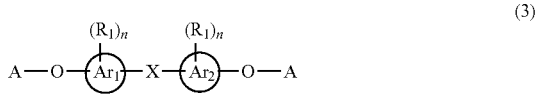
(3)

(In formula (3), $Ar_1$, $Ar_2$, $R_1$, n, X, and A are as defined in formulae (1) and (2).)

Specific examples and preferred examples of $Ar_1$, $Ar_2$, $R_1$, n, and X in formula (3) above are the same as those in formula (1), and specific examples and preferred examples of A in formula (3) above are the same as those in formula (2). The aromatic bis ether compound represented by formula (3) above in the case where X is a single bond, which is particularly preferred, is represented by formula (3-1) below.

[Chem. 17]

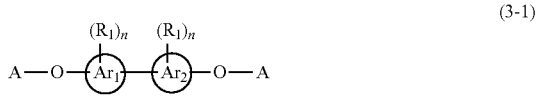
(3-1)

(In the formula, $Ar_1$, $Ar_2$, $R_1$, n, and A are as defined in formulae (1) and (2).)

Furthermore, when the group represented by A is more specifically shown, the aromatic bis ether compound is represented by, for example, formula (3-1-2a), formula (3-1-2b), formula (3-1-2c), or formula (3-1-2d) below.

[Chem. 18]

(3-1-2a)

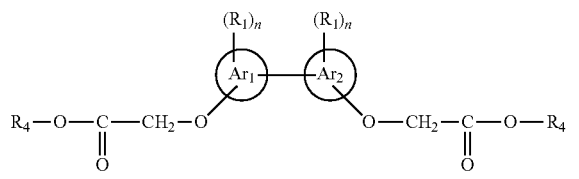

(3-1-2b)

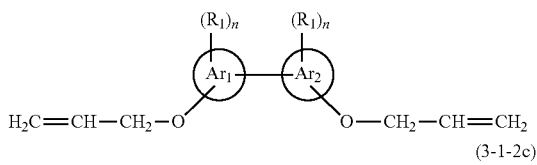

(3-1-2c)

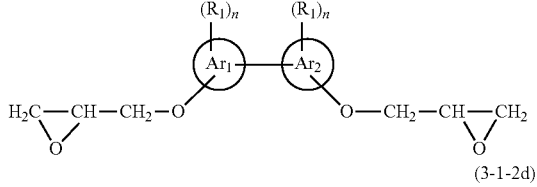

(3-1-2d)

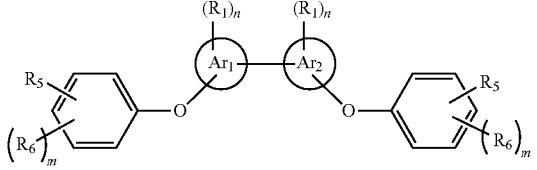

The compound represented by formula (3-1) above in the case where $Ar_1$ and $Ar_2$ are each a phenylene group is represented by formula (3-2) below.

[Chem. 19]

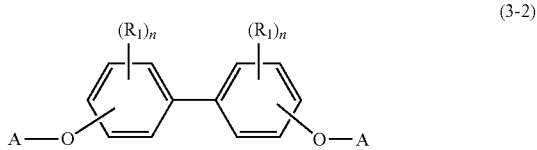
(3-2)

(In the formula, $R_1$, n, and A are as defined in formulae (1) and (2).)

Furthermore, when the group represented by A is more specifically shown, the aromatic bis ether compound is represented by, for example, formula (3-2-2a), formula (3-2-2b), formula (3-2-2c), or formula (3-2-2d) below.

[Chem. 20]

(3-2-2a)

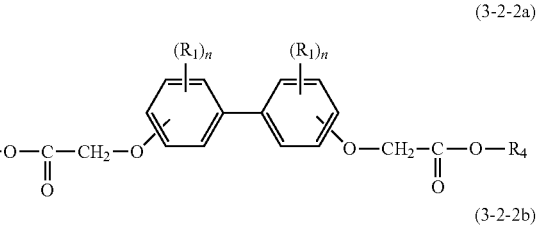

(3-2-2b)

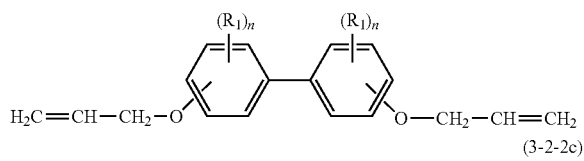

(3-2-2c)

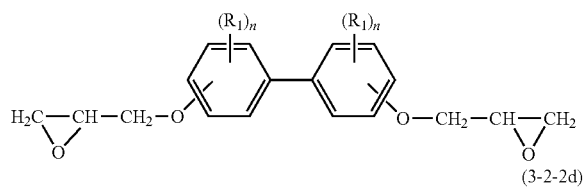

(3-2-2d)

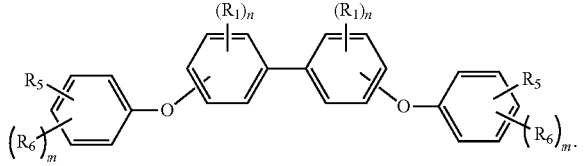

(In the formulae, $R_1$, n, $R_4$, $R_5$, $R_6$, and m are as defined in formulae (1), (2a), and (2d).)

Specific examples of the compound represented by formula (3-2-2a) above include 4,4'-bis(2-methoxycarbonylmethoxy)-biphenyl, 4,4'-bis(2-ethoxycarbonylmethoxy)-biphenyl, 4,4'-bis(2-methoxycarbonylmethoxy)-3,3'-dimethyl-biphenyl, 4,4'-bis(2-ethoxycarbonylmethoxy)-3,3'-dimethyl-biphenyl, 4,4'-bis(2-methoxycarbonylmethoxy)-3,3'-diethyl-biphenyl, 4,4'-bis(2-ethoxycarbonylmethoxy)-3,3'-diethyl-biphenyl, 4,4'-bis(2-methoxycarbonylmethoxy)-3,3',5,5'-tetramethyl-biphenyl, 4,4'-bis(2-ethoxycarbonylmethoxy)-3,3',5,5'-tetramethyl-biphenyl, 4,4'-bis(2-methoxycarbonylmethoxy)-3,3',6,6'-tetramethyl-biphenyl, 4,4'-bis (2-ethoxycarbonylmethoxy)-3,3',6,6'-tetramethyl-biphenyl, 4,4'-bis(2-methoxycarbonylmethoxy)-3,3'-dimethyl-5,5'-di-t-butyl-biphenyl, 4,4'-bis(2-ethoxycarbonylmethoxy)-3,3'-dimethyl-5,5'-di-t-butyl-biphenyl, 4,4'-bis(2-methoxycarbonylmethoxy)-3,3',5,5'-tetra-t-butylbiphenyl, and 4,4'-bis(2-ethoxycarbonylmethoxy)-3,3',5,5'-tetra-t-butylbiphenyl.

Among them, 4,4'-bis(2-methoxycarbonylmethoxy)-biphenyl, 4,4'-bis(2-ethoxycarbonylmethoxy)-biphenyl, 4,4'-bis(2-methoxycarbonylmethoxy)-3,3'-dimethyl-biphenyl, 4,4'-bis(2-ethoxycarbonylmethoxy)-3,3'-dimethyl-biphenyl, 4,4'-bis(2-methoxycarbonylmethoxy)-3,3',5,5'-tetramethyl-biphenyl, and 4,4'-bis(2-ethoxycarbonylmethoxy)-3,3',5,5'-tetramethyl-biphenyl are preferred.

The compound represented by formula (3-1) above in the case where $Ar_1$ and $Ar_2$ are each a naphthylene group, which is particularly preferred, is represented by formula (3-3) below.

[Chem. 21]

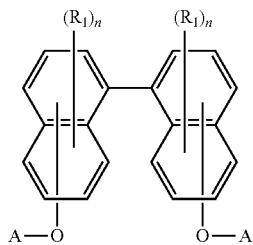

(3-3)

(In the formula, $R_1$, n, and A are as defined in formulae (1) and (2).)

Furthermore, when the group represented by A in formula (3-1) above is more specifically shown, formula (3-1) above is, for example, a compound represented by formula (3-3-2a), formula (3-3-2b), formula (3-3-2c), or formula (3-3-2d) below.

[Chem. 22]

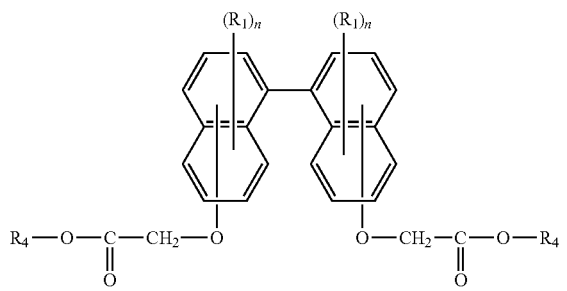

(3-3-2a)

(3-3-2b)

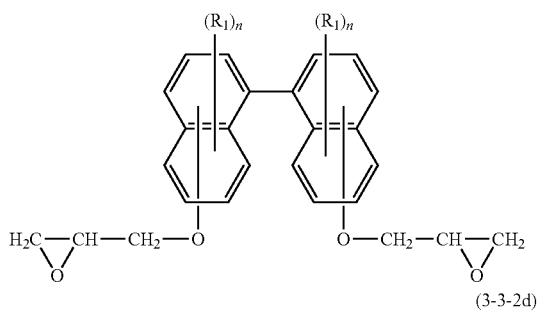

(3-3-2c)

(3-3-2d)

(In the formulae, $R_1$ and n are as defined in formula (1), $R_4$ is as defined in formula (2a), and $R_5$, $R_6$, and m are as defined in formula (2d).)

Among them, the compound represented by formula (3-3-2a) above where A is a group represented by formula (2a) above is particularly preferred, as in formula (2) above.

The compound represented by formula (3-1) above in the case where $Ar_1$ and $Ar_2$ are each a biphenylene group is, for example, a compound represented by formula (3-4-2a), formula (3-4-2b), formula (3-4-2c), or formula (3-4-2d) below.

[Chem. 23]

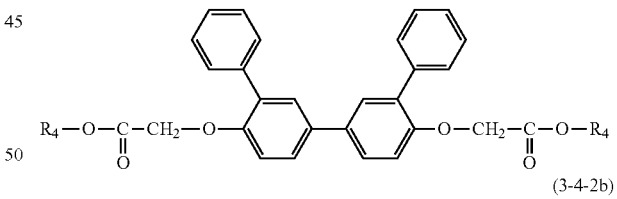

(3-4-2a)

(3-4-2b)

(3-4-2c)

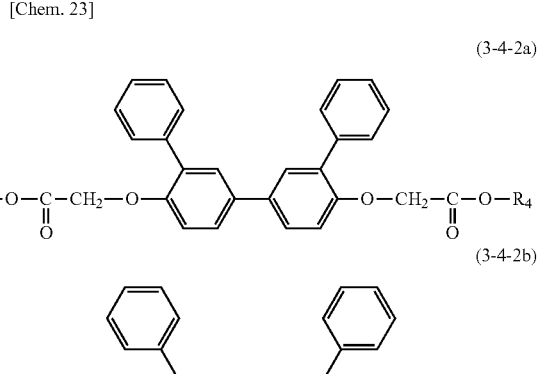

-continued (3-4-2d)

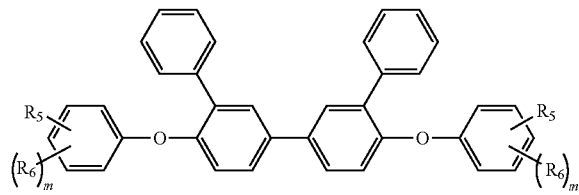

(In the formulae, $R_4$, $R_5$, $R_6$, and m are as defined in formulae (2a) and (2d).)

Among the aromatic bis ether compounds (3) in the present invention, the compound represented by formula (3-3-2a) above is particularly preferred, and specific examples include 2,2'-bis(2-methoxycarbonylmethoxy)-1,1'-binaphthyl, 2,2'-bis(2-ethoxycarbonylmethoxy)-1,1'-binaphthyl (compound represented by formula (B) below), 2,2'-bis(2-propoxycarbonylmethoxy)-1,1'-binaphthyl, and 2,2'-bis(2-pentoxycarbonylmethoxy)-1,1'-binaphthyl.

[Chem. 24]

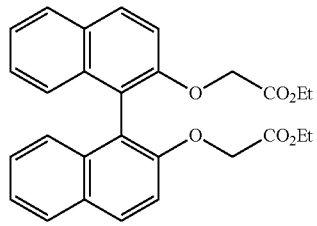

(B)

<Amount of Raw Material Used>

In the production method of the present invention, the amount of the halide (2) used is not particularly limited as long as its theoretical value is 2.0 mol or more relative to 1 mol of the aromatic dihydroxy compound (1) used as a raw material, and is typically 2.0 mol or more, preferably in the range of 2.0 to 3.0 mol, more preferably in the range of 2.0 to 2.8 mol, still more preferably in the range of 2.2 to 2.5 mol.

<Catalyst>

In the production method of the present invention, the reaction is preferably carried out in the presence of an iodide salt such as an alkali metal iodide or an ammonium iodide in order to further improve the reaction efficiency.

Specific examples include potassium iodide, sodium iodide, tetraalkylammonium iodide, tetraarylammonium iodide, and tetraarylalkylammonium iodide. These may be used alone or as a mixture of two or more.

The amount of the iodide salt used is preferably in the range of 2 to 20 parts by weight, more preferably in the range of 2 to 10 parts by weight, still more preferably in the range of 2 to 5 parts by weight, relative to 100 parts by weight of the aromatic dihydroxy compound (1) used as a raw material.

<Reaction Solvent>

As a solvent that can be used in the production method of the present invention, an aprotic polar solvent is preferably used. Specific examples include linear aliphatic ketones having 5 to 8 carbon atoms, such as diethyl ketone (5 carbon atoms), methyl isobutyl ketone (6 carbon atoms), methyl amyl ketone (7 carbon atoms), and methylhexyl ketone (8 carbon atoms), linear nitrile solvents having 2 to 6 carbon atoms, such as acetonitrile and propanenitrile, ether solvents such as diethyl ether and tetrahydrofuran (THF), ester solvents such as ethyl acetate, dimethylformamide, and dimethylsulfoxide. Among them, from the viewpoint of the reaction rate, linear aliphatic ketones having 5 to 8 carbon atoms, linear nitrile solvents having 2 to 6 carbon atoms, dimethylformamide, and dimethylsulfoxide are more preferred, and for reasons of low water solubility and facilitation of water washing treatment for removing a base and the like used in the reaction, linear aliphatic ketones having 5 to 8 carbon atoms are still more preferred, and linear aliphatic ketones having 6 or 7 carbon atoms are particularly preferred. These solvents may be used alone or as a mixture of two or more.

The amount of solvent used in the reaction is preferably in the range of 150 to 500 parts by weight, more preferably in the range of 150 to 350 parts by weight, still more preferably 150 to 250 parts by weight, relative to 100 parts by weight of the aromatic dihydroxy compound (1).

<Base>

In the production method of the present invention, the aromatic dihydroxy compound (1) is preferably phenoxidized (or naphtoxidized) with a base to have higher nucleophilicity before being reacted with the halide (2). The base is not particularly limited, and, for example, alkali metal carbonates such as lithium carbonate, sodium carbonate, and potassium carbonate, alkali metal hydrogen carbonates such as sodium hydrogen carbonate and potassium hydrogen carbonate, alkali metal hydroxides such as lithium hydroxide, sodium hydroxide, and potassium hydroxide, and organic bases such as triethylamine and pyridine are suitable for use. Among them, sodium carbonate and potassium carbonate are preferred. The amount of the base used is preferably 2.0 to 2.5 mol, more preferably 2.05 to 2.15 mol, relative to 1 mol of the aromatic dihydroxy compound (1).

<Reaction Temperature>

The reaction temperature at which the aromatic dihydroxy compound (1) and the halide (2) are reacted with each other is typically in the range of 50° C. to 160° C., preferably in the range of 70° C. to 130° C., more preferably in the range of 90° C. to 110° C. A high reaction temperature is not preferred because the yield of the aromatic bis ether compound (3), which is the target compound, decreases particularly due to hydrolysis or the like. A low reaction temperature is not preferred because the reaction rate slows down. The reaction is typically carried out under normal pressure, but depending on the boiling point of the aliphatic ketone solvent having 5 to 8 carbon atoms used, the reaction may be carried out under pressure or reduced pressure so that the reaction temperature falls within the above range.

<Amount of Water>

The amount of water in a reaction solution in the production method of the present invention is 0.01 wt % or more and 1.5 wt % or less relative to the amount of the aromatic dihydroxy compound (1), and when the amount of water is in this range, the aromatic bis ether compound (3), which is the target compound, can be produced in good reaction yield. The upper limit of the amount of water is more preferably 1.3 wt % or less, still more preferably 1.0 wt % or less, particularly preferably 0.5 wt % or less.

According to the method of the present invention, a monoether compound represented by formula (3') below, which is a reaction intermediate of the target compound represented by formula (3) above and is an impurity, can be produced from the raw materials and consumed into the target compound in a facilitated manner, and the target compound can be obtained efficiently and in high reaction yield.

[Chem. 25]

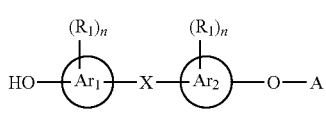

(3')

(In formula (3'), Ar$_1$, Ar$_2$, R$_1$, n, X, and A are as defined in formulae (1) and (2).)

The compound represented by formula (3') above in the case where X is a direct bond, which is particularly preferred, is represented by formula (3'-1) below.

[Chem. 26]

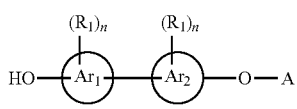

(3'-1)

(In formula (3'-1), Ar$_1$, Ar$_2$, R$_1$, n, and A are as defined in formulae (1) and (2).)

Furthermore, the compound in the case where Ar$_1$ and Ar$_2$ are each a naphthylene group, which is particularly preferred, is represented by formula (3'-3) below.

[Chem. 27]

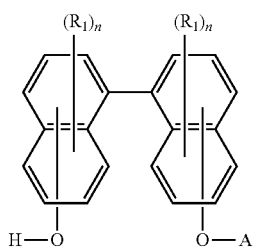

(3'-3)

(In formula (3'-3), R$_1$, n, and A are as defined in formulae (1) and (2).)

The compound in the case where A is a group represented by formula (2a) is represented by formula (3'-3-2a) below.

[Chem. 28]

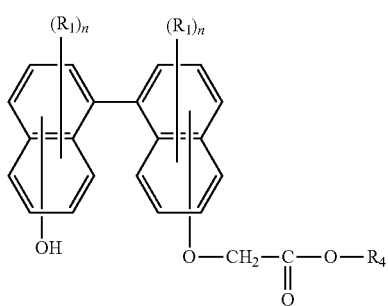

(3'-3-2a)

(In formula (3'-3-2a), R$_1$, n, are R$_4$ are as defined in formulae (1) and (2a).)

Specifically, for example, the reaction intermediate corresponding to the compound represented by formula (B) above is a compound represented by formula (B') below.

[Chem. 29]

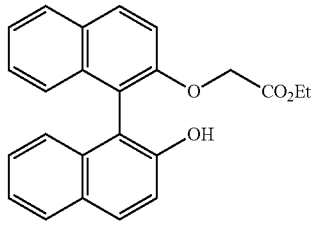

(B')

In addition, if the amount of water in a reaction solution is large particularly when a reaction between the halide (2) in the case where A in formula (2) is a group represented by formula (2a) above and the compound represented by formula (1) above is carried out, the ester bond in the group undergoes hydrolysis to produce a hydrolysate as an impurity as shown by the following reaction formula, resulting in a lower reaction yield. However, when the amount of water in the reaction solution is in the specific range in the present invention, the reaction yield of the target compound significantly improves, which is particularly useful.

[Chem. 30]

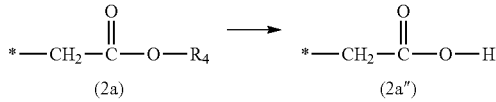

As a result of undergoing hydrolysis as described above, for example, the compound represented by formula (3-3-2a) among the compounds represented by formula (3) above becomes a compound represented by formula (3-3-2a") below, contributing to the decrease in the reaction yield.

[Chem. 31]

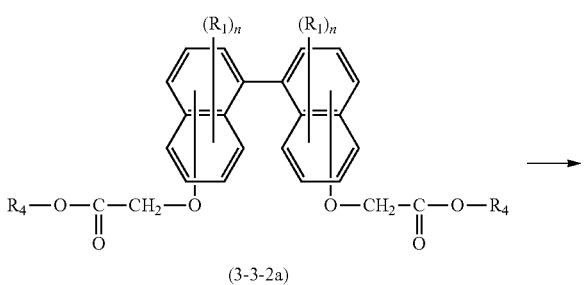

(3-3-2a)

-continued

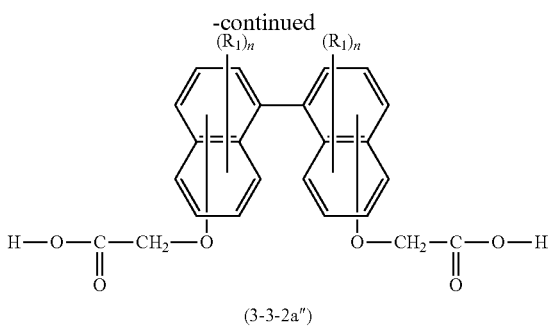

(3-3-2a″)

(In formula (3-3-2a″), $R_1$ and n are as defined in formula (1).)

Specifically, for example, the hydrolysate corresponding to the compound represented by formula (B) above is a compound represented by formula (B″) below.

[Chem. 32]

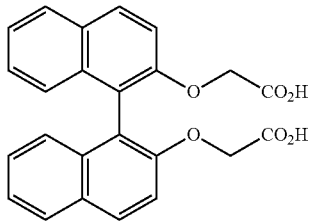

(B″)

Examples of methods for controlling the amount of water in the reaction solution to be in a specific range in the reaction between the aromatic dihydroxy compound (1) and the halide (2) include, in the case where the amount of water is large, dehydration by distillation operation, dehydration using a dehydrating agent, and dehydration by membrane separation, such as pervaporation membrane separation or vapor permeation membrane separation, using a membrane (e.g., zeolite membrane) capable of separating water from a reaction mixture. Among them, dehydration by distillation operation is preferred because of its simple industrial operation. The conditions under which the distillation operation is carried out vary depending on the type of solvent used. The pressure may be typically atmospheric pressure or reduced pressure, and when the distillation operation is carried out under reduced pressure, the pressure is preferably in the range of 40 to 80 KPa. The temperature is typically in the range of 70° C. to 120° C., preferably in the range of 90° C. to 100° C.

On the other hand, in the case where the amount of water is small, addition of water to the reaction solution may be employed.

<Reaction Completion>

The endpoint of the reaction can be determined by liquid chromatography or gas chromatography analysis. The endpoint of the reaction is preferably defined as the time point at which the unreacted aromatic dihydroxy compound (1) has disappeared and the increase of the aromatic bis ether compound (3), which is the target compound, is no longer observed. Although the reaction time varies depending on the reaction conditions such as reaction temperature, the reaction is typically completed in about 1 to 30 hours.

After completion of the reaction, water is added to the reaction solution, the mixture is stirred, and then the resultant is left to stand to separate an aqueous layer. This water washing operation is performed twice or more, whereby the inorganic salt in the reaction solution can be removed. The amount of water used in one water washing operation is preferably in the range of 150 to 600 parts by weight, more preferably in the range of 200 to 400 parts by weight, relative to 100 parts by weight of the aromatic dihydroxy compound (1) used. The temperature in the operation is preferably in the range of 60° C. to 100° C., more preferably in the range of 70° C. to 90° C. The stirring may be performed in any manner as long as an oil layer is sufficiently brought into contact with an aqueous layer, and although the time required varies depending on the apparatus, about 30 minutes is usually sufficient. It is preferable to purify and isolate the aromatic bis ether compound (3), which is the target compound, from the oil layer left after the water washing operation. For example, the aromatic bis ether compound (3), which is the target compound, can be obtained by performing post-treatment operations such as separation by crystallization, filtration, distillation, column chromatography, etc. according to a conventional method after the water washing operation. To further increase the purity, purification by distillation, recrystallization, or column chromatography may be performed according to a conventional method.

EXAMPLES

The present invention will now be described more specifically with reference to Examples, but it should be noted that the present invention is not limited to these Examples.

The method of analysis is as follows.

<Method of Analysis>

1. Determination of Target Compound Concentration in Reaction Solution, Reaction Yield, and Reaction Endpoint Measuring apparatus: high-performance liquid chromatography analyzer (manufactured by Shimadzu Corporation)

Pump: LC-20AD
Column oven: CTO-20A
Detector: SPD-20A
Column: HALO-C18
Oven temperature: 50° C.
Flow rate: 0.7 mL/min
Mobile phase: (A) acetonitrile, (B) 0.1 vol % aqueous phosphoric acid solution
Gradient conditions: (A) % by volume (time from start of analysis)
30% (0 min)→100% (12 min)→100% (15 min)
Detection wavelength: 280 nm After the measurement was performed under the above conditions, the reaction yield (%) of target compounds obtained in Examples and Comparative Examples was calculated using a liquid chromatography calibration curve of the target compound.

For impurities, their content was calculated as an area percentage in the results of the measurement under the above conditions, provided that the peak of a reaction solvent (methyl isobutyl ketone) was excluded.

2. Method of Analyzing Amount of Water

Measuring instrument: Karl Fischer MKS-520 (manufactured by Kyoto Electronics Manufacturing Co., Ltd.)

Titration was performed using 3 mg of AQUAMICRON Titrant SS as a titrant, and the amount of water was measured by volumetric titration.

Example 1

In a four-necked flask, 30 g of 1,1′-binaphthalene-2,2′-diol (A), 75 g of methyl isobutyl ketone, 30.4 g of potassium carbonate, and 0.6 g of potassium iodide were placed, heated to 100° C., and stirred at this temperature for two hours. After the stirring, 30 g of methyl isobutyl ketone was distilled out under a reduced pressure of 60 to 70 KPa at a temperature of 90° C. to 100° C. The amount of water in the system at this time was 0.3 wt % relative to the amount of 1,1'-binaphthalene-2,2'-diol used. After a mixed solution of 28.2 g of ethyl chloroacetate and 0.3 g of N-methylpyrrolidone was prepared, the mixed solution was added dropwise while maintaining the temperature of the reaction solution at 90° C. to 100° C. The reaction formula at this time is shown below. After stirring for 10 hours, the reaction yield of the target compound 2,2'-bis(2-ethoxycarbonylmethoxy)-1,1'-binaphthyl (B) was determined to be 99.1% using the high-performance liquid chromatography calibration curve. For impurities, the content of a reaction intermediate (B') of (B) was determined to be 0.2%, and the content of 2,2'-bis (2-carboxymethoxy)-1,1'-binaphthyl (B"), a hydrolysate of (B), was determined to be 0.3%.

[Chem. 33]

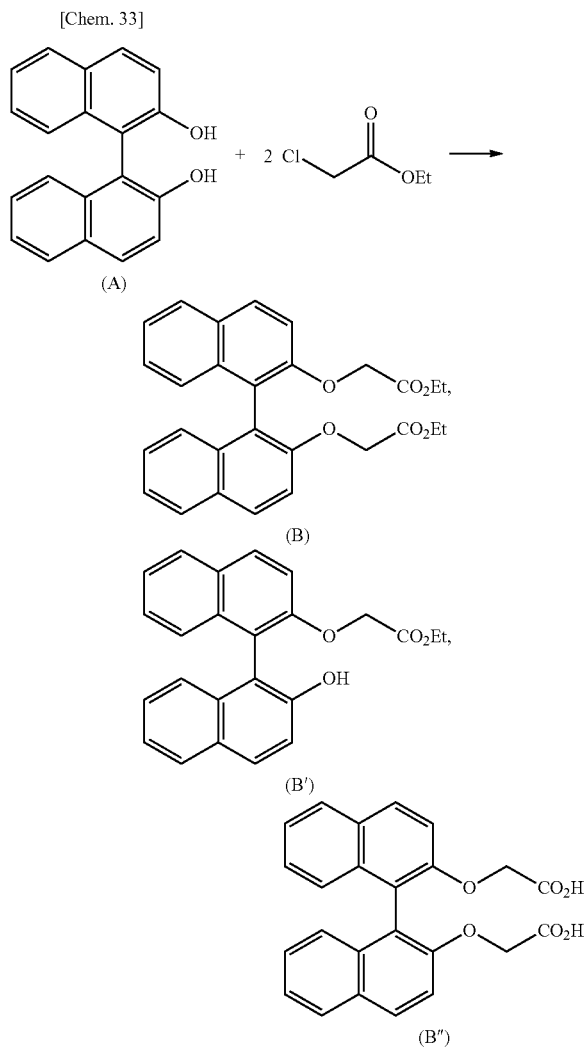

Example 2

In a four-necked flask, 30 g of 1,1'-binaphthalene-2,2'-diol (A), 75 g of methyl isobutyl ketone, 30.4 g of potassium carbonate, and 0.6 g of potassium iodide were placed, heated to 100° C., and stirred at this temperature for two hours. The amount of water in the system at this time was 0.6 wt % relative to the amount of 1,1'-binaphthalene-2,2'-diol used. After a mixed solution of 28.2 g of ethyl chloroacetate and 0.3 g of N-methylpyrrolidone was prepared, the mixed solution was added dropwise while maintaining the temperature of the reaction solution at 90° C. to 100° C. After stirring for 10 hours, the reaction yield of the target compound (B) was determined to be 98.2% using the high-performance liquid chromatography calibration curve. For impurities, the content of the reaction intermediate (B') was determined to be 0.4%, and the content of the hydrolysate (B") was determined to be 1.1%.

Example 3

In a four-necked flask, 30 g of 1,1'-binaphthalene-2,2'-diol (A), 75 g of methyl isobutyl ketone, 30.4 g of potassium carbonate, and 0.6 g of potassium iodide were placed, heated to 100° C., and stirred at this temperature for two hours. Water was added thereto so that the amount of water in the system was 1.3 wt % relative to the amount of 1,1'-binaphthalene-2,2'-diol used. After a mixed solution of 28.2 g of ethyl chloroacetate and 0.3 g of N-methylpyrrolidone was prepared, the mixed solution was added dropwise while maintaining the temperature of the reaction solution at 90° C. to 100° C. After stirring for 10 hours, the reaction yield of the target compound (B) was determined to be 93.8% using the high-performance liquid chromatography calibration curve. For impurities, the content of the reaction intermediate (B') was determined to be 2.9%, and the content of the hydrolysate (B") was determined to be 1.5%.

Comparative Example 1

In a four-necked flask, 30 g of 1,1'-binaphthalene-2,2'-diol (A), 150 g of methyl isobutyl ketone, 30.4 g of potassium carbonate, and 0.6 g of potassium iodide were placed, heated to 100° C., and stirred at this temperature for two hours. Water was added thereto so that the amount of water in the system was 2.0 wt % relative to the amount of 1,1'-binaphthalene-2,2'-diol used. After the addition, a mixed solution of 28.2 g of ethyl chloroacetate and 0.3 g of N-methylpyrrolidone was prepared, and the mixed solution was then added dropwise while maintaining the temperature of the reaction solution at 90° C. to 100° C. After stirring for 10 hours, the reaction yield of the target compound (B) was determined to be 83.8% by high-performance liquid chromatography. For impurities, the content of the reaction intermediate (B') was determined to be 3.3%, and the content of the hydrolysate (B") was determined to be 5.9%.

Comparative Example 2

In a four-necked flask, 30 g of 1,1'-binaphthalene-2,2'-diol (A), 150 g of methyl isobutyl ketone, 30.4 g of potassium carbonate, and 0.6 g of potassium iodide were placed, heated to 100° C., and stirred at this temperature for two hours. Water was added thereto so that the amount of water in the system was 3.0 wt % relative to the amount of 1,1'-binaphthalene-2,2'-diol used. After a mixed solution of 28.2 g of ethyl chloroacetate and 0.3 g of N-methylpyrrolidone was prepared, the mixed solution was added dropwise while maintaining the temperature of the reaction solution at 90° C. to 100° C. After stirring for 10 hours, the reaction yield of the target compound (B) was determined to be 76.7% using the high-performance liquid chromatography calibration curve. For impurities, the content of the reaction intermediate (B') was determined to be 8.4%, and the content of the hydrolysate (B") was determined to be 4.1%.

Comparative Example 3

The reaction was carried out in the same manner as in Comparative Example 1 except that water was added so that the amount of water in the system was 6.2 wt % relative to the amount of 1,1'-binaphthalene-2,2'-diol used. The reaction yield of the target compound (B) was determined to be 68.6% using the high-performance liquid chromatography calibration curve. For impurities, the content of the reaction intermediate (B') was determined to be 15.8%, and the content of the hydrolysate (B") was determined to be 6.7%.

For Examples 1 to 3 and Comparative Examples 1 to 3 described above, the amount of water in the reaction system relative to the amount of the compound represented by general formula (1) used, the reaction yield of the target compound (B), and the contents of the reaction intermediate (B') and the hydrolysate (B"), which are impurities, are shown in Table 1 below and FIG. 1.

TABLE 1

| | Amount of water in reaction system | Target compound (B) reaction yield | Reaction intermediate (B') content | Hydrolysate (B") content |
|---|---|---|---|---|
| Example 1 | 0.3 wt % | 99.1% | 0.2% | 0.3% |
| Example 2 | 0.6 wt % | 98.2% | 0.4% | 1.1% |
| Example 3 | 1.3 wt % | 93.8% | 2.9% | 1.5% |
| Comparative Example 1 | 2.0 wt % | 83.8% | 3.3% | 5.9% |
| Comparative Example 2 | 3.0 wt % | 76.7% | 8.4% | 4.1% |
| Comparative Example 3 | 6.2 wt % | 68.6% | 15.8% | 6.7% |

In Comparative Examples 1 to 3, in which the production method of the present invention was not used, the reaction yield was low for industrial production of the compound represented by general formula (3). This is due to the slow progress of the etherification reaction, which can be seen from the high reaction intermediate contents. In addition, the hydrolysate was produced in large amounts.

On the other hand, it was revealed that when the production method of the present invention was used, the reaction yield was significantly improved to exceed 90% because the progress of the etherification reaction was promoted. Is was also revealed that the formation of the hydrolysate was significantly suppressed.

Thus, the production method of the present invention is very useful in industrial production.

The invention claimed is:
1. A method for producing an aromatic bis ether compound represented by formula 3-3 below, wherein in a reaction, in the presence of a linear aliphatic ketone having 5 to 8 carbon atoms, between an aromatic dihydroxy compound 1 represented by formula 1-3 below and a halide 2 represented by formula 2 below, an amount of water in a reaction solution is 0.01 wt % or more and 1.5 wt % or less relative to an amount of the aromatic dihydroxy compound 1 in the reaction solution,

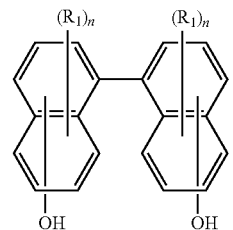

1-3 wherein each $R_1$ independently represents a linear alkyl group having 1 to 6 carbon atoms or a branched alkyl group having 3 to 6 carbon atoms, or a cyclic alkyl group having 5 or 6 carbon atoms, and each n independently represents an integer of 0 to 4,
wherein Y represents a chlorine atom, and A represents a group represented by formula 2a below,

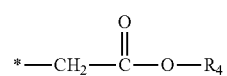

2a wherein $R_4$ is a linear alkyl group having 1 to 6 carbon atoms or a branched alkyl group having 3 to 6 carbon atoms, and * represents a bonding position,

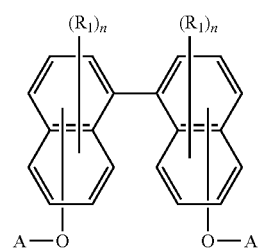

3-3 wherein $R_1$ and n are as defined in formula 3, and A is as defined in formula 2.

* * * * *

UNITED STATES PATENT AND TRADEMARK OFFICE
CERTIFICATE OF CORRECTION

PATENT NO. : 12,398,088 B2
APPLICATION NO. : 17/640793
DATED : August 26, 2025
INVENTOR(S) : Takeru Suto Page 1 of 1

It is certified that error appears in the above-identified patent and that said Letters Patent is hereby corrected as shown below:

In the Claims

At Column 22, Line 27, in Claim 1, after the term "an integer of 0 to 4", the chemical formula --Y-A 2-- should be inserted.

At Column 22, Line 53, in Claim 1, the term "formula 3" should be "formula 1-3".

Signed and Sealed this
Thirtieth Day of September, 2025

John A. Squires
*Director of the United States Patent and Trademark Office*